United States Patent

US 12,256,142 B2

Yamaguchi

(10) Patent No.: US 12,256,142 B2
(45) Date of Patent: Mar. 18, 2025

(54) CONTROL DEVICE AND MEDICAL OBSERVATION SYSTEM

(71) Applicant: Sony Olympus Medical Solutions Inc., Tokyo (JP)

(72) Inventor: Kazuhiro Yamaguchi, Tokyo (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 649 days.

(21) Appl. No.: 17/433,603

(22) PCT Filed: Feb. 5, 2020

(86) PCT No.: PCT/JP2020/004438
§ 371 (c)(1),
(2) Date: Aug. 25, 2021

(87) PCT Pub. No.: WO2020/195204
PCT Pub. Date: Oct. 1, 2020

(65) Prior Publication Data
US 2022/0141376 A1      May 5, 2022

(30) Foreign Application Priority Data
Mar. 22, 2019   (JP) ................................. 2019-055706

(51) Int. Cl.
*H04N 23/66*      (2023.01)
*A61B 34/00*      (2016.01)
(Continued)

(52) U.S. Cl.
CPC ............ *H04N 23/66* (2023.01); *A61B 34/25* (2016.02); *A61B 90/20* (2016.02); *G10L 15/22* (2013.01);
(Continued)

(58) Field of Classification Search
CPC ...... H04N 23/66; H04N 23/69; H04N 23/695; A61B 34/25; A61B 90/20; A61B 90/25;
(Continued)

(56) References Cited

U.S. PATENT DOCUMENTS 4,912,388 A * 3/1990 Tanaka ................. G05B 19/408
250/221
6,425,858 B1   7/2002 Minami
(Continued)

FOREIGN PATENT DOCUMENTS

EP      3447764 A1 * 2/2019 ............. G10L 15/02
EP      3632365 A1   4/2020
(Continued)

OTHER PUBLICATIONS

International Search Report and Written Opinion mailed on Mar. 24, 2020, received for PCT Application PCT/JP2020/004438, Filed on Feb. 5, 2020, 10 pages including English Translation.

*Primary Examiner* — Daniel C Washburn
*Assistant Examiner* — Penny L Caudle
(74) *Attorney, Agent, or Firm* — XSENSUS LLP

(57) ABSTRACT

Provided is a control device that electrically controls a medical observation apparatus configured to capture an image of an observation target and includes a voice recognition section, a recognized-information processing section, a switch input reception section, and a control section. The voice recognition section recognizes a voice inputted from outside. Based on a result of recognition by the voice recognition section, the recognized-information processing section determines processing to be executed by the medical observation apparatus. The switch input reception section receives an input of an operation signal based on an operation performed on a switch. Upon detecting a first operation signal received by the switch input reception section or upon acquiring information regarding processing determined by (Continued)

the recognized-information processing section, the control section causes the voice recognition section to start voice recognition processing and causes the medical observation apparatus to execute the processing determined by the recognized-information processing section.

8 Claims, 8 Drawing Sheets

(51) Int. Cl.
    *A61B 90/20*     (2016.01)
    *A61B 90/25*     (2016.01)
    *G10L 15/22*     (2006.01)
    *H04N 23/69*     (2023.01)
    *H04N 23/695*     (2023.01)
    *A61B 17/00*     (2006.01)

(52) U.S. Cl.
    CPC ........... *H04N 23/69* (2023.01); *H04N 23/695* (2023.01); *A61B 2017/00203* (2013.01); *A61B 90/25* (2016.02); *A61B 2560/0493* (2013.01); *G10L 2015/223* (2013.01)

(58) Field of Classification Search
    CPC .. A61B 2017/00203; A61B 2560/0493; A61B 2017/00973; A61B 2034/2059; A61B 2090/306; A61B 2090/508; G10L 15/22; G10L 2015/223

See application file for complete search history.

(56) References Cited

U.S. PATENT DOCUMENTS

| | | | |
|---|---|---|---|
| 2013/0325479 A1* | 12/2013 | Krueger | G06F 1/1632 |
| | | | 704/275 |
| 2018/0338813 A1 | 11/2018 | Taguchi | |
| 2019/0015175 A1 | 1/2019 | Tamura | |
| 2019/0053857 A1 | 2/2019 | Sugie | |

FOREIGN PATENT DOCUMENTS

| | | | |
|---|---|---|---|
| JP | 62-166312 A | 7/1987 | |
| JP | 2000116670 A | 4/2000 | |
| JP | 2001-108906 A | 4/2001 | |
| JP | 2004-24869 A | 1/2004 | |
| JP | 2008284273 A | 11/2008 | |
| JP | 2017225502 A | 12/2017 | |
| WO | 2017/061294 A1 | 4/2017 | |
| WO | WO-2018097065 A1 | 5/2018 | |
| WO | 2018/159155 A1 | 9/2018 | |
| WO | 2018/216302 A1 | 11/2018 | |

* cited by examiner

CONTROL DEVICE AND MEDICAL OBSERVATION SYSTEM

CROSS-REFERENCE TO RELATED APPLICATIONS

The present application is based on PCT filing PCT/JP2020/004438, filed Feb. 5, 2020, which claims priority to JP 2019-055706, filed Mar. 22, 2019, the entire contents of each are incorporated herein by reference.

TECHNICAL FIELD

The present disclosure relates to a control device that controls a medical observation apparatus for observing, for example, microscopic parts of an observation target. The present disclosure also relates to a medical observation system.

BACKGROUND ART

In the past, an optical microscope system has been known as a medical observation system for observing microscopic parts of an observation target, such as the brain or heart of a patient, during surgery on the microscopic parts. The existing optical microscope system includes a support section and a microscope section. The support section includes a plurality of arm sections and has a total of six degrees of freedom of movement, namely, three degrees of freedom of translation and three degrees of freedom of rotation. The microscope section is disposed on the leading end of the support section and is provided with an imaging element and a magnifying optical system for magnifying the microscopic parts.

Incidentally, it is demanded that the above optical microscope system be controllable by the voice of a surgeon without requiring the surgeon to look away from a surgical site or a monitor. However, functions requiring continuous drive, such as zoom ratio and focal length adjustments and field-of-view movement, are difficult to be controlled fully by the voice alone. There is a known technology that addresses the above control problem by using a combination of voice input means and continuous input means such as a foot switch (refer, for example, to PTL 1). This technology enables the surgeon to control the functions requiring continuous drive, which are not easily controlled by the voice alone.

CITATION LIST

Patent Literature

[PTL 1]
JP 2004-24869A

SUMMARY

Technical Problems

However, according to PTL 1, a microphone is connected to a voice recognition device while a foot switch is connected to a control device for controlling a microscope section. As the microphone and the foot switch are connected to different devices, the resulting device configuration is complicated.

Further, after a function is called by voice recognition, an operation is inputted by the foot switch or other input means. Therefore, a significant amount of time is required for the execution of the operation.

The present disclosure is made in view of the above circumstances. An object of the present disclosure is to provide a control device and a medical observation system that make it possible to complete voice recognition and processing based on the voice recognition within a short period of time by using a simple configuration, and easily stop the processing.

Solution to Problems

In order to solve the above problems and accomplish the above object, according to the present disclosure, there is provided a control device that electrically controls a medical observation apparatus configured to capture an image of an observation target and includes a voice recognition section, a recognized-information processing section, a switch input reception section, and a control section. The voice recognition section recognizes a voice inputted from outside. Based on a result of recognition by the voice recognition section, the recognized-information processing section determines processing to be executed by the medical observation apparatus. The switch input reception section receives an input of an operation signal based on an operation performed on a switch. Upon detecting a first operation signal received by the switch input reception section or upon acquiring information regarding the processing determined by the recognized-information processing section, the control section causes the voice recognition section to start voice recognition processing and causes the medical observation apparatus to execute the processing determined by the recognized-information processing section. Further, upon detecting a second operation signal, the control section stops the processing to be executed by the medical observation apparatus.

According to the present disclosure described above, the control device is configured such that the switch input reception section receives, as the operation signal, an input of an input value based on the operation performed on the switch, and that, upon detecting a first change in the input value received by the switch input reception section, the control section causes the voice recognition section to start voice recognition processing and causes the medical observation apparatus to execute the processing determined by the recognized-information processing section, and, upon detecting a second change in the input value, the control section stops the processing to be executed by the medical observation apparatus.

According to the present disclosure described above, the control device is configured such that the first operation signal and the second operation signal function as different operation signals and correspond to different operations performed on the switch.

According to the present disclosure described above, the control device is configured such that the first operation signal and the second operation signal function as the same operation signal and correspond to similar operations performed on the switch.

According to the present disclosure described above, the control device is configured such that, in a case where the input value is changed from an initial value of the switch to a value other than the initial value, the control section starts the voice recognition processing and causes the medical observation apparatus to execute processing, and that, in a case where the input value is changed to the initial value, the control section stops the processing to be executed by the medical observation apparatus.

According to the present disclosure described above, the control device is configured such that the control section changes driving speed of the medical observation apparatus according to the operation signal received by the switch input reception section.

According to the present disclosure described above, the control device is configured such that, in a case where the input value is changed from the initial value during a preset period after the processing to be executed by the medical observation apparatus is stopped due to the input value change to the initial value, the control section causes the medical observation apparatus to execute processing that is reverse of the preceding processing performed before the stop.

According to the present disclosure described above, the control device is configured such that, in a case where the input value is changed from the initial value of the switch to a value other than the initial value, the control section starts the voice recognition processing and causes the medical observation apparatus to execute processing, and that, in a case where the input value is changed again from the initial value to a value other than the initial value, the control section stops the processing to be executed by the medical observation apparatus.

According to the present disclosure described above, the control device is configured such that the switch input reception section receives an input of an operation signal that is outputted upon depression of the switch, that the control section causes the medical observation apparatus to continuously execute the processing determined by the recognized-information processing section while the switch is continuously depressed, and that, in a case where the switch is released, the control section causes the medical observation apparatus to stop the processing determined by the recognized-information processing section.

According to the present disclosure described above, the control device is configured such that, in a case where the result of voice recognition by the voice recognition section agrees with first recognized information, the control section enables later voice recognition processing, and that, in a case where the result of voice recognition by the voice recognition section agrees with second recognized information, the control section disables later voice recognition processing.

According to the present disclosure described above, the control device is configured such that, in a case where the result of voice recognition by the voice recognition section agrees with first recognized information, the control section enables later voice recognition processing, and that, after a preset period of time elapses since the voice recognition processing by the voice recognition section is enabled, the control section disables a voice recognition result other than the first recognized information.

According to the present disclosure described above, the control device is configured such that, based on the result of recognition by the voice recognition section, the recognized-information processing section determines a direction in which the medical observation apparatus moves an imaging area, and that, based on the movement direction determined by the recognized-information processing section, the control section causes the medical observation apparatus to move the imaging area.

According to the present disclosure described above, the control device is configured such that, based on the result of recognition by the voice recognition section, the recognized-information processing section determines image magnifying power of the medical observation apparatus, and that, based on the magnifying power determined by the recognized-information processing section, the control section changes the image magnifying power of the medical observation apparatus.

According to the present disclosure, there is provided a medical observation system including an imaging section, a support section, a voice recognition section, a recognized-information processing section, a switch, a switch input reception section, and a control section. The imaging section is able to capture a magnified image of an observation target. The support section includes a plurality of arm sections and a plurality of joint sections connecting the plurality of arm sections and supports the imaging section at a leading end of the support section. The voice recognition section recognizes a voice inputted from outside. The recognized-information processing section determines, based on a result of recognition by the voice recognition section, processing to be executed by the imaging section or the support section. The switch outputs an operation signal based on an operation performed on the switch. The switch input reception section receives an input from the switch. Upon detecting a first operation signal received by the switch input reception section or upon acquiring information regarding processing determined by the recognized-information processing section, the control section causes the voice recognition section to start voice recognition processing and causes the imaging section or the support section to execute the processing determined by the recognized-information processing section. Upon detecting a second operation signal, the control section stops the processing to be executed by the imaging section or the support section.

Advantageous Effects of Invention

The present disclosure makes it possible to complete voice recognition and processing based on the voice recognition within a short period of time by using a simple configuration, and easily stop the processing.

DESCRIPTION OF EMBODIMENTS

Best modes (hereinafter referred to as embodiments) for implementing the present invention will now be described with reference to the accompanying drawings. It should be noted that the drawings are merely schematic and different from each other in dimensional relation and ratio.

First Embodiment

Figure 1:
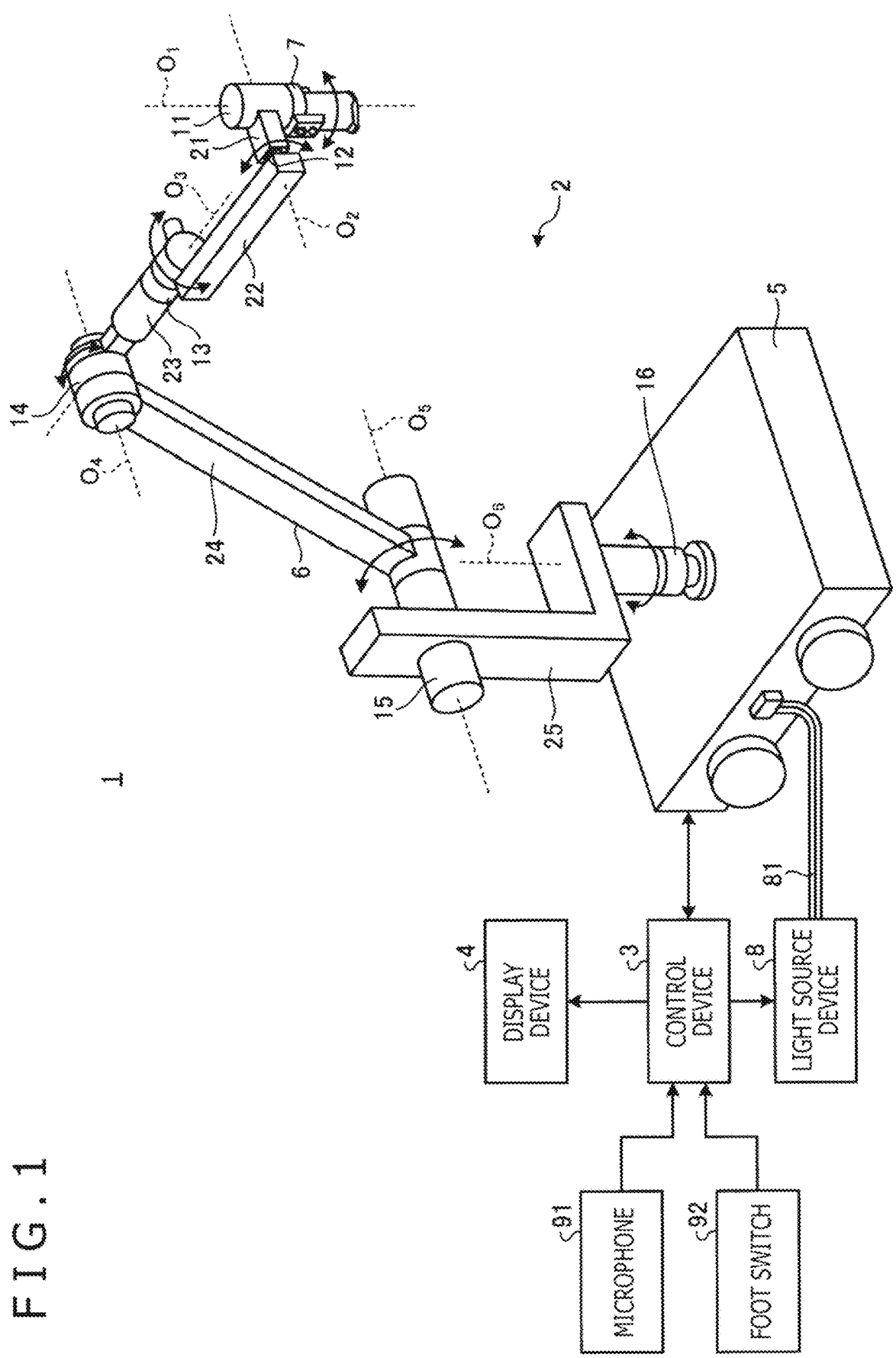
FIG. 1 is a perspective view illustrating an external configuration of a medical observation system according to a first embodiment.

FIG. 1 is a diagram illustrating a configuration of a medical observation system according to a first embodiment. A medical observation system 1 depicted in FIG. 1 includes a medical observation apparatus (hereinafter referred to as the observation apparatus) 2, a control device, 3, and a display device 4. The observation apparatus 2 is capable of functioning as a microscope that captures a magnified image of a microstructure of an observation target. The control device 3 provides integrated control of operations of the medical observation system 1. The display device 4 displays an image captured by the observation apparatus 2.

The observation apparatus 2 includes a base section 5, a support section 6, and a microscope section 7. The base section 5 is capable of moving over a floor surface. The support section 6 is supported by the base section 5. The microscope section 7 is columnar in shape, disposed on the leading end of the support section 6, and configured to capture a magnified image of microscopic parts of the observation target. Further, the observation apparatus 2 is connected to a light source device 8. The light source device 8 supplies illumination light to the observation apparatus 2 through a light guide 81 including, for example, an optical fiber. The light source device 8 emits the illumination light, under the control of the control device 3.

In the observation apparatus 2, transmission cables including a signal wire (coaxial cable) for signal transmission between the control device 3 and the microscope section 7, a light guide cable for guiding the illumination light from the light source device 8 to the microscope section 7, and various other cables are disposed between the base section 5 and the microscope section 7. The cables are disposed along the support section 6. The coaxial cable, which is formed by a thin wire, is smaller in diameter than the light guide cable.

The support section 6 includes a first joint section 11, a first arm section 21, a second joint section 12, a second arm section 22, a third joint section 13, a third arm section 23, a fourth joint section 14, a fourth arm section 24, a fifth joint section 15, a fifth arm section 25, and a sixth joint section 16.

The support section 6 includes four sets of two arm sections and one joint section. The joint section pivotally couples one arm section (positioned toward a leading end) to the other arm section (positioned toward a base end). More specifically, the four sets include a set having the first arm section 21, the second joint section 12, and the second arm section 22, a set having the second arm section 22, the third joint section 13, and the third arm section 23, a set having the third arm section 23, the fourth joint section 14, and the fourth arm section 24, and a set having the fourth arm section 24, the fifth joint section 15, and the fifth arm section 25.

The first joint section 11 is retained by the first arm section 21 in a state where the leading end of the first joint section 11 pivotally retains the microscope section 7 and the base end is fastened to the leading end of the first arm section 21. The first joint section 11 has a cylindrical shape and retains the microscope section 7 in such a manner as to let it pivot around a first axis $O_1$. The first axis $O_1$ is the central axis in the height direction. The first arm section 21 has a shape extended from a lateral surface of the first joint section 11 in a direction orthogonal to the first axis $O_1$.

The second joint section 12 is retained by the second arm section 22 in a state where the leading end of the second joint section 12 pivotally retains the first arm section 21 and the base end is fastened to the leading end of the second arm section 22. The second joint section 12 has a cylindrical shape and retains the first arm section 21 in such a manner as to let it pivot around a second axis $O_2$. The second axis $O_2$ is the central axis in the height direction and orthogonal to the first axis $O_1$. The second arm section 22 is shaped substantially like the letter L and is coupled to the second joint section 12 at an end of an L-shaped vertical line portion.

The third joint section 13 is retained by the third arm section 23 in a state where the leading end of the third joint section 13 pivotally retains an L-shaped horizontal line portion of the second arm section 22 and the base end is fastened to the leading end of the third arm section 23. The third joint section 13 has a cylindrical shape and retains the second arm section 22 in such a manner as to let it pivot around a third axis $O_3$. The third axis $O_3$ is the central axis in the height direction, orthogonal to the second axis $O_2$, and parallel to the direction in which the second arm section 22 is extended. The leading end of the third arm section 23 is cylindrical in shape, and the base end has a through-hole that is formed in a direction orthogonal to the height direction of the cylindrically shaped leading end. The third joint section 13 is pivotally retained by the fourth joint section 14 via the through-hole.

The fourth joint section 14 is retained by the fourth arm section 24 in a state where the leading end of the fourth joint section 14 pivotally retains the third arm section 23 and the base end is fastened to the fourth arm section 24. The fourth joint section 14 has a cylindrical shape and retains the third arm section 23 in such a manner as to let it pivot around a fourth axis $O_4$. The fourth axis $O_4$ is the central axis in the height direction and orthogonal to the third axis $O_3$.

The fifth joint section 15 is mounted in a state where the leading end pivotally retains the fourth arm section 24 and the base end is fastened to the fifth arm section 25. The fifth joint section 15 has a cylindrical shape and retains the fourth arm section 24 in such a manner as to let it pivot around a fifth axis $O_5$. The fifth axis $O_5$ is the central axis in the height direction and parallel to the fourth axis $O_4$. The fifth arm section 25 has an L-shaped portion and a rod-shaped portion. The rod-shaped portion is extended downward from an L-shaped horizontal line portion. The base end of the fifth joint section 15 is mounted on an end of an L-shaped vertical line portion of the fifth arm section 25.

The sixth joint section 16 is mounted in a state where the leading end pivotally retains the fifth arm section 25 and the base end is fastened to the upper surface of the base section 5. The sixth joint section 16 has a cylindrical shape and retains the fifth arm section 25 in such a manner as to let it pivot around a sixth axis $O_6$. The sixth axis $O_6$ is the central axis in the height direction and orthogonal to the fifth axis $O_5$. The base end of the rod-shaped portion of the fifth arm section 25 is mounted on the leading end of the sixth joint section 16.

The support section 6 having the above-described configuration provides a total of six degrees of freedom of movement in the microscope section 7, namely, three degrees of freedom of translation and three degrees of freedom of rotation.

The first to sixth joint sections 11 to 16 have electromagnetic brakes that respectively prohibit the microscope section 7 and the first to fifth arm sections 21 to 25 from pivoting. When an arm operation switch (described later) attached to the microscope section 7 is depressed, the electromagnetic brakes are released to permit the microscope section 7 and the first to fifth arm sections 21 to 25 to pivot. It should be noted that air brakes may be applied instead of the electromagnetic brakes.

The joint sections each incorporate an encoder and an actuator in addition to the above-mentioned electromagnetic brake. When incorporated, for example, in the first joint section 11, the encoder detects the angle of rotation around the first axis $O_1$. The actuator includes an electric motor, such as a servomotor, and is driven, under the control of the control device 3 to rotate the associated joint section by a predetermined angle. The angle of rotation in each joint section is set as a value necessary, for example, for the microscope section 7 by the control device 3 according to the angle of rotation around each of the rotation axes (the first to sixth axes $O_1$ to $O_6$). As described above, the joint sections having an active drive mechanism, such as the actuator, forms an actively rotating axis of rotation when the drive of the actuator is controlled.

The microscope section 7 has a cylindrical housing and includes an imaging section, an arm operation switch, and a lever. The imaging section captures a magnified image of an observation target. The arm operation switch receives an operation input that releases the electromagnetic brakes of the first to sixth joint sections 11 to 16 in order to permit the joint sections to pivot. The lever is able to change the magnifying power of the imaging section 72 and the focal length to the observation target.

The imaging section includes two imaging elements that are formed by a CCD (Charge Coupled Device) or a CMOS (Complementary Metal Oxide Semiconductor). The imaging elements generate imaging signals that have a mutual parallax and are used for three-dimensional image generation. The imaging signals are outputted as digital signals. An alternative configuration may be adopted to incorporate only one imaging element and generate imaging signals for two-dimensional image generation.

The imaging section further includes, for example, an optical system for guiding light to the imaging elements, a magnifying optical system for changing the image magnifying power (zoom ratio), and a shutter for controlling the exposure time. Additionally, the imaging section incorporates an actuator for moving optical system lenses and an encoder. The optical system in the imaging section is able to change the zoom ratio, adjust the focal length, and change some other imaging settings by allowing the lenses to move, under the control of the control device 3.

Further, the microscope section 7 is provided with the arm operation switch, which is a pushbutton switch. While the arm operation switch is depressed by a user, the electromagnetic brakes of the first to sixth joint sections 11 to 16 are released.

The control device 3 receives an imaging signal outputted from the observation apparatus 2 and performs predetermined signal processing on the received imaging signal to generate three-dimensional image data for display purposes. It should be noted that the control device 3 may be installed in the base section 5 and used as an integral part of the observation apparatus 2.

The control device 3 is connected to a microphone 91 and a foot switch 92. The microphone 91 inputs a user's voice. The foot switch 92 is operated, that is, depressed, by a user's foot in order to input a signal based on the depression.

Figure 2:
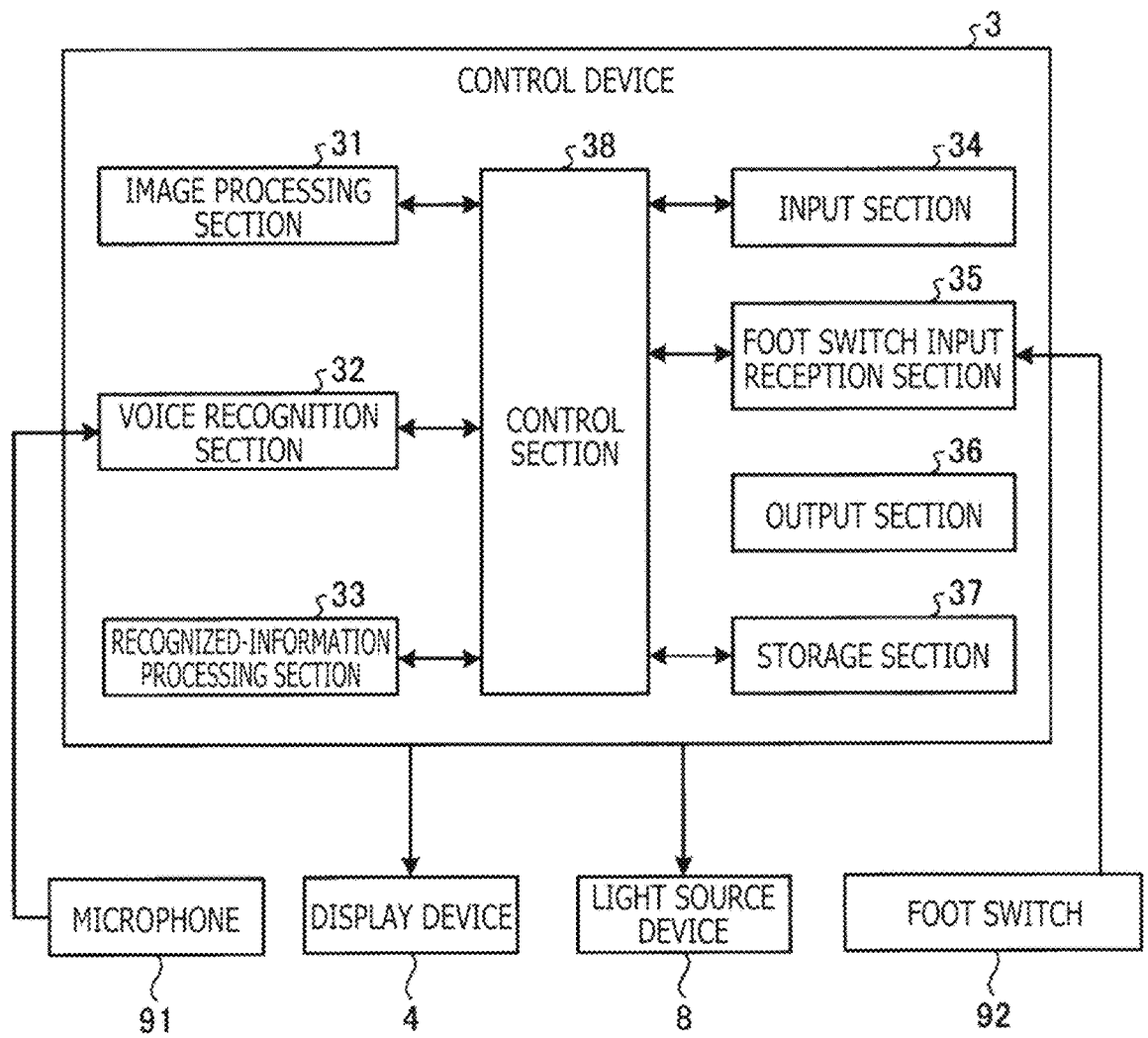
FIG. 2 is a block diagram illustrating a configuration of a control device in the medical observation system according to the first embodiment.

FIG. 2 is a block diagram illustrating a configuration of the control device in the medical observation system according to the first embodiment. The control device 3 includes an image processing section 31, a voice recognition section 32, a recognized-information processing section 33, an input section 34, a foot switch input reception section 35, an output section 36, a storage section 37, and a control section 38. It should be noted that the control device 3 may additionally include, for example, a power supply section (not depicted) that generates a power supply voltage for driving the observation apparatus 2, the control device 3, the microphone 91, and the foot switch 92, and supplies the generated power supply voltage to each section of the control device 3 and to the observation apparatus 2.

The image processing section 31 performs noise removal or other signal processing and, if necessary, A/D conversion signal processing, on the imaging signal outputted from the microscope section 7. Based on the signal-processed imaging signal, the image processing section 31 generates an image signal that the display device 4 uses for display purposes. The image processing section 31 executes predetermined signal processing on the imaging signal to generate, for display purposes, the image signal including a signal corresponding to a subject image. In this instance, the image processing section 31 performs various kinds of known image processing such as detection processing, interpolation processing, color correction processing, color enhancement processing, and contour enhancement processing. The image processing section 31 outputs the generated image signal to the display device 4.

Further, the image processing section 31 may additionally include an AF processing section and an AF computing section. The AF processing section outputs a predetermined AF evaluation value of each frame according to an inputted frame imaging signal. The AF computing section performs AF computation processing in order to select the most suitable frame or focus lens position as the in-focus position according to the AF evaluation value of each frame, which is outputted from the AF processing section.

The voice recognition section 32 detects a voice that is inputted to the microphone 91 by the user, and performs recognition processing on the inputted voice. The voice recognition section 32 compares the feature amount of the voice inputted to the microphone 91 with a recognition model stored in the storage section 37 and associated with a recognition result, and receives a language series as the recognition result. More specifically, in a case where "Rightward" is inputted to the microphone 91, the voice recognition section 32 recognizes an inputted utterance as "Rightward" according to the feature amount and the recognition model, and then outputs the recognition result to the recognized-information processing section 33.

The recognized-information processing section 33 acquires the recognition result from the voice recognition section 32 and determines the processing based on the recognition result. The recognized-information processing section 33 references the storage section 37 to determine the processing based on the recognition result. The recognized-information processing section 33 outputs, to the control section 38, a processing description determined based on the recognition result.

For example, in a case where "Rightward" is indicated by the recognition result, the control section 38 moves the imaging area of the microscope section 7 rightward. When the microscope section 7 moves, the imaging area used by the microscope section 7 moves. In this instance, the orientation (rightward, leftward, upward, or downward) of the microscope section 7 with respect to its imaging area is preset based on the relation between the imaging elements and the display orientation of the display device 4. Without changing the operating distance and zoom ratio of the microscope section 7, the control section 38 drives the individual joint sections to move the position of the microscope section 7 in such a manner that only the imaging area moves rightward.

Further, in a case where "Magnify" or "Reduce" is indicated by the recognition result, the control section 38 drives the magnifying optical system of the microscope section 7. For example, in a case where the "Magnify" is indicated by the recognition result, the control section 38 provides control to increase the zoom ratio of the magnifying optical system. This changes the magnifying power at which imaging is performed by the microscope section 7.

The input section 34 is implemented by using a user interface, such as a keyboard, a mouse, or a touch panel, and configured to receive an input of various kinds of information.

The foot switch input reception section 35 detects that the foot switch 92 is depressed by the user, and then receives an input from the foot switch 92. The foot switch input reception section 35 inputs an operation signal based on the depression to the control section 38.

The output section 36 is implemented, for example, by a speaker, a printer, or a display, and configured to output various kinds of information.

The storage section 37 is implemented by a semiconductor memory, such as a flash memory or a DRAM (Dynamic Random Access Memory), and configured to record, for example, a voice recognition table and a processing table. The voice recognition table is created by associating communication information data (e.g., communication format information) with voice feature amounts and recognition models. The processing table is created by associating voice recognition results and processing descriptions. It should be noted that the storage section 37 may record, for example, various programs to be executed by the control section 38.

The control section 38 provides control such as drive control of individual component sections including the control device 3 and the observation apparatus 2, and input/output control of information with respect to the individual component sections. The control section 38 references the communication information data (e.g., communication format information) recorded in the storage section 37, generates control signals accordingly, and transmits the generated control signals to the observation apparatus 2.

It should be noted that the control section 38 generates a sync signal and a clock for the microscope section 7 and the control device 3. The sync signal (e.g., a sync signal for dictating the time of imaging) and clock for the microscope section 7 are transmitted to the microscope section 7 through an undepicted cable. The microscope section 7 is then driven based on the transmitted sync signal and clock.

The image processing section 31, the voice recognition section 32, the recognized-information processing section 33, the foot switch input reception section 35, and the control section 38, which are described above, are each implemented by using a dedicated processor such as one of various computing circuits for executing specific functions. For example, the dedicated processor may be a general-purpose processor or an ASIC (Application Specific Integrated Circuit), such as a CPU (Central Processing Unit) having an internal memory (not depicted) in which a program is recorded. Further, the dedicated processor may be an FPGA (Field Programmable Gate Array (not depicted)), a type of programmable integrated circuit. It should be noted that, in a case where an FPGA is adopted for configuration, the FPGA, which is a programmable integrated circuit, may be configured by using configuration data read from a memory incorporated to store the configuration data.

The display device 4 receives the three-dimensional image data generated by the control device 3 and displays a three-dimensional image corresponding to the three-dimensional image data. The display device 4 described above is provided with a display panel that includes liquid crystal or organic EL (Electro Luminescence).

It should be noted that an output device for outputting information by using, for example, a speaker or a printer may be incorporated in addition to the display device 4.

The following provides an overview of surgery that is performed by using the medical observation system 1 configured as described above. In a case where the user, that is, a surgeon, performs surgery on the head of a patient, the surgeon wears three-dimensional image viewing eyeglasses, grips the microscope section 7, and moves the microscope section 7 to a desired position while holding down the arm operation switch of the microscope section 7 and viewing a three-dimensional image displayed by the display device 4. Upon determining the imaging area of the microscope section 7, the surgeon releases the arm operation switch. This activates the electromagnetic brakes of the first to sixth joint sections 11 to 16 to fix the imaging area of the microscope section 7. Thereafter, for example, the surgeon adjusts the magnifying power and the focal length to the observation target. As the display device 4 displays a three-dimensional image, the surgeon is able to three-dimensionally grasp a surgical site through the three-dimensional image. Thereafter, the surgeon operates the microphone 91 and the foot switch 92 as needed to adjust the position of the microscope section 7, the magnifying power, and the focal length.

Figure 3:
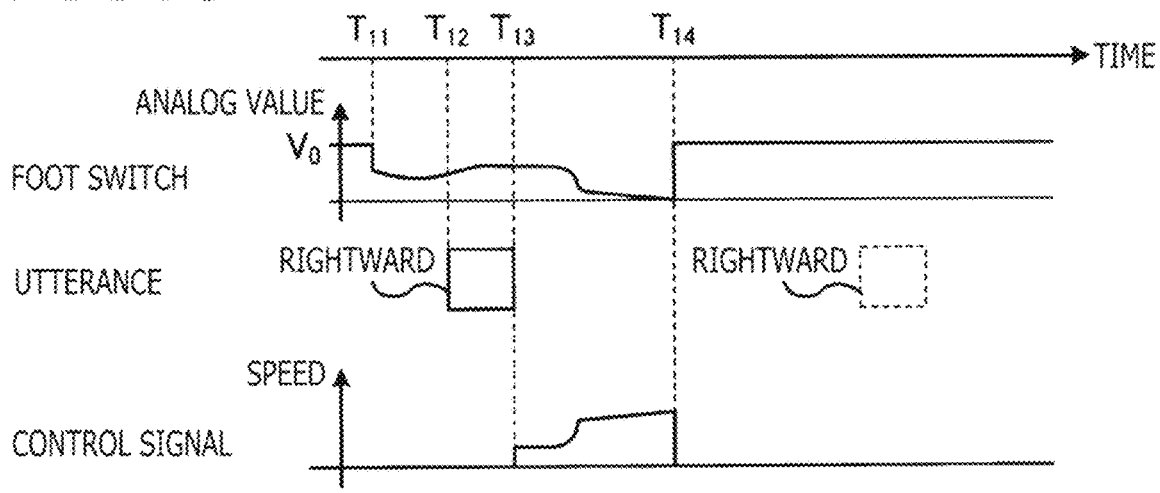
FIG. 3 is a timing diagram illustrating an example of a driving process that is performed by using the medical observation system according to the first embodiment.

Operation processing performed by the control device 3 with respect to the microphone 91 (voice recognition) and the foot switch 92 will now be described with reference to FIG. 3. FIG. 3 is a timing diagram illustrating an example of a driving process that is performed by using the medical observation system according to the first embodiment. The timing diagram of FIG. 3 indicates an input value (analog value) inputted by the foot switch 92, an utterance, and a control signal (speed).

The first embodiment starts voice input recognition processing when the foot switch 92 is depressed, and executes processing based on the result of recognition. The processing based on the recognition result is maintained while the foot switch 92 is depressed.

More specifically, upon detecting that the foot switch 92 is depressed (stepped on), the foot switch input reception section 35 outputs, to the control section 38, an analog value based on the amount of depression. In the example of FIG. 3, the user steps on the foot switch 92 at time $T_{11}$. In this instance, an increase in the depression amount of the foot switch 92 decreases the analog value from an analog value (initial value $V_0$) used in a case where the foot switch 92 is not stepped on.

Upon detecting that the foot switch 92 is depressed at time $T_{11}$, the control section 38 starts performing voice recognition processing by using the microphone 91. The user steps on the foot switch 92, and then inputs a voice to the microphone 91. In the example depicted in FIG. 3, the user inputs "Rightward" to the microphone 91.

When "Rightward" is inputted to the microphone 91 at time $T_{12}$, during a period until time $T_{13}$, the voice recognition section 32 performs recognition processing, and the recognized-information processing section 33 determines the processing to be executed. In the first embodiment, a voice signal "Rightward" corresponds to a first operation signal. The first operation signal is a signal generated upon voice input.

The recognized-information processing section 33 determines the processing to be executed. In this instance, when the determined processing is for moving the microscope section 7 rightward, the control section 38 outputs, after time $T_{13}$, control signals to various sections to drive various joint sections as needed to move the microscope section 7 rightward. In this instance, the control section 38 provides control such that a driving speed for moving the microscope section 7 increases with an increase in the depression amount of the foot switch 92 (with a decrease in the analog value).

It should be noted that, in a case where an inputted utterance is recognized as "Rightward" and a different utterance is inputted while the microscope section 7 moves rightward between time $T_{13}$ and time $T_{14}$, and the inputted different utterance is, for example, recognized as "Upward," the control section 38 may perform, for example, one of the following processes:

Ignores a voice input other than the initial one received after the foot switch 92 is stepped on.
Switches to control for moving the microscope section 7 "Upward."
Moves the microscope section 7 obliquely "Upper Rightward."

Thereafter, when the foot switch 92 is released at time $T_{14}$, the microscope section 7 stops moving. Even if the user utters a voice (e.g., "Rightward") toward the microphone 91 after time $T_{14}$ while the foot switch 92 is not stepped on, neither voice recognition processing nor recognized-information processing is executed. In the first embodiment, a second operation signal corresponds to a detection signal that is obtained when the initial value $V_0$ is detected when the foot switch 92 is released. The first embodiment provides control by using the first operation signal based on voice input and the second operation signal based on the operation of the foot switch 92.

As described above, the first embodiment is configured such that, in a case where the analog value inputted when the foot switch 92 is stepped on changes to a value other than the initial value $V_0$, the control section 38 detects a first change and starts voice recognition processing. Meanwhile, in a case where the analog value returns to the initial value $V_0$ when the foot switch 92 is released, the control section 38 detects a second change and stops processing based on voice recognition.

The first embodiment, which has been described above, receives a voice input from the microphone 91 in a state where the foot switch 92 is depressed, and executes processing based on the result of recognition. Thereafter, the first embodiment maintains the processing based on the recognition result while the foot switch 92 is depressed, and stops the processing when the foot switch 92 is released. According to the first embodiment, the processing performed during a period between the start of voice recognition and the stop of the processing is collectively controlled within the control device 3 (which controls the microscope section 7 and the support section 6) upon depression of the foot switch 92. This makes it possible to adopt a simple configuration, complete the processing ranging from voice recognition to driving based on the voice recognition within a short period of time, and easily stop the processing.

It should be noted that the first embodiment has been described with reference to an example where the movement speed of the microscope section 7 varies with the amount of depression of the foot switch 92. However, the microscope section 7 may alternatively move at a predetermined constant speed. Further, the foot switch 92 may output a digital value, such as a binary or ternary value, instead of the analog value depicted in FIG. 3.

Further, the first embodiment has been described with reference to an example where the control device 3 includes the foot switch input reception section 35, the voice recognition section 32, the recognized-information processing section 33, and the storage section 37. Alternatively, however, some or all of the foot switch input reception section 35, the voice recognition section 32, the recognized-information processing section 33, and the storage section 37 may be separated from the control device 3.

Second Embodiment

Figure 4:
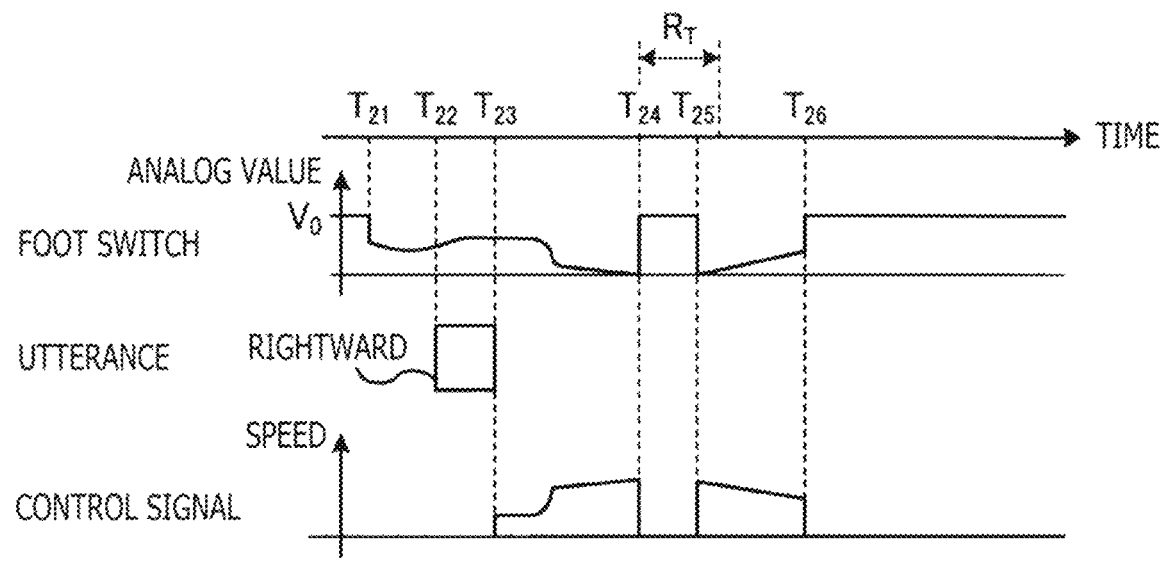
FIG. 4 is a timing diagram illustrating an example of the driving process that is performed by using the medical observation system according to a second embodiment.

A second embodiment will now be described with reference to FIG. 4. FIG. 4 is a timing diagram illustrating an example of the driving process that is performed by using the medical observation system according to the second embodiment. The configuration of the medical observation system according to the second embodiment is the same as that of the earlier-described medical observation system 1 according to the first embodiment, and will not be redundantly described. The following describes the difference in processing from the first embodiment.

Upon detecting that the foot switch 92 is depressed (stepped on), the foot switch input reception section 35 outputs an analog value based on the depression amount to the control section 38. In the example of FIG. 4, the user steps on the foot switch 92 at time $T_{21}$. In this instance, an increase in the depression amount of the foot switch 92 decreases the analog value from an analog value (initial value $V_0$) used in a case where the foot switch 92 is not stepped on.

Upon detecting that the foot switch 92 is depressed at time $T_{21}$, the control section 38 starts performing voice recognition processing by using the microphone 91. The user steps on the foot switch 92, and then inputs a voice to the microphone 91. In the example depicted in FIG. 4, the user inputs "Rightward" to the microphone 91.

When "Rightward" is inputted to the microphone 91 at time $T_{22}$, during a period until time $T_{23}$, the voice recognition section 32 performs recognition processing, and the recognized-information processing section 33 determines the processing to be executed.

The recognized-information processing section 33 determines the processing to be executed. In this instance, when the determined processing is for moving the microscope section 7 rightward, the control section 38 outputs, after time $T_{23}$, control signals to various sections to drive various joint sections as needed to move the microscope section 7 rightward. In this instance, the control section 38 provides control such that the speed for moving the microscope section 7 increases with an increase in the depression amount of the foot switch 92 (with a decrease in the analog value).

Thereafter, when the foot switch 92 is released at time $T_{24}$, the microscope section 7 stops moving.

When the foot switch 92 is stepped on again at time $T_{25}$ within a preset range of time (period $R_T$) after time $T_{24}$, the control section 38 resumes moving the microscope section 7. In this instance, the control section 38 moves the microscope section 7 ("Leftward" in this case) in a direction opposite to the direction in which the microscope section 7 moved before foot switch re-depression. Even when moving the microscope section 7 in the opposite direction, the control section 38 provides control such that the speed for moving the microscope section 7 increases with an increase in the depression amount of the foot switch 92 (with a decrease in the analog value).

The range of time (period $R_T$) within which the microscope section 7 moves in the opposite direction upon re-depression of the foot switch 92 is set, for example, to a value between 0.5 seconds or more and 2.0 seconds or less. The period $R_T$ may be set after a wait time for avoiding recognition error due to chattering.

Thereafter, when the foot switch 92 is released at time $T_{26}$, the microscope section 7 stops moving.

The second embodiment, which has been described above, receives a voice input from the microphone 91 in a state where the foot switch 92 is depressed, and executes processing based on the result of recognition. Thereafter, the second embodiment maintains the processing based on the recognition result while the foot switch 92 is depressed, and stops the processing when the foot switch 92 is released. Further, when the foot switch 92 is depressed again within the preset range of time (period $R_T$), the second embodiment executes a process that is the reverse of the preceding process. According to the second embodiment, the processing performed during a period between the start of voice recognition and the stop of the processing is collectively controlled within the control device 3 (which controls the microscope section 7 and the support section 6) upon depression of the foot switch 92. This makes it possible to adopt a simple configuration, complete the processing ranging from voice recognition to driving based on the voice recognition within a short period of time, and easily stop the processing. Additionally, the second embodiment executes a reverse process upon re-depression of the foot switch 92. Therefore, the processing can be fine-tuned simply by operating the foot switch 92.

Third Embodiment

Figure 5:
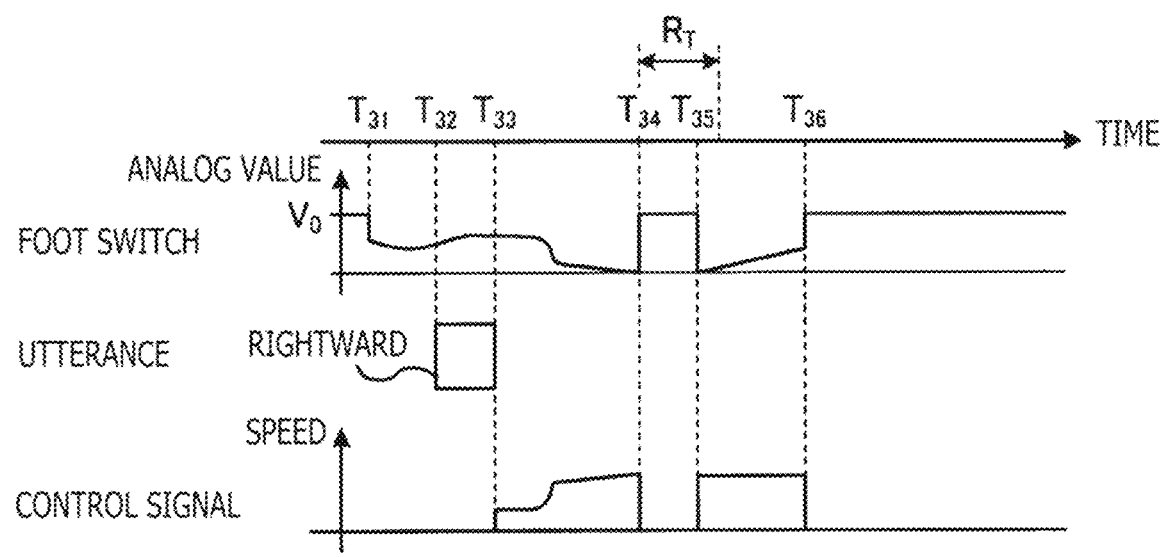
FIG. 5 is a timing diagram illustrating an example of the driving process that is performed by using the medical observation system according to a third embodiment of the present disclosure.

A third embodiment will now be described with reference to FIG. 5. FIG. 5 is a timing diagram illustrating an example of the driving process that is performed by using the medical observation system according to the third embodiment. The configuration of the medical observation system according to the third embodiment is the same as that of the earlier-described medical observation system 1 according to the first embodiment, and will not be redundantly described. The following describes the difference in processing from the first embodiment.

Upon detecting that the foot switch 92 is depressed (stepped on), the foot switch input reception section 35 outputs an analog value based on the depression amount to the control section 38. In the example of FIG. 5, the user steps on the foot switch 92 at time $T_{31}$. In this instance, an increase in the depression amount of the foot switch 92 decreases the analog value from an analog value (initial value $V_0$) used in a case where the foot switch 92 is not stepped on.

Upon detecting that the foot switch 92 is depressed at time $T_{31}$, the control section 38 starts performing voice recognition processing by using the microphone 91. The user steps on the foot switch 92, and then inputs a voice to the microphone 91. In the example depicted in FIG. 5, the user inputs "Rightward" to the microphone 91.

When "Rightward" is inputted to the microphone 91 at time $T_{32}$, during a period until time $T_{23}$, the voice recognition section 32 performs recognition processing, and the recognized-information processing section 33 determines the processing to be executed.

The recognized-information processing section 33 determines the processing to be executed. In this instance, when the determined processing is for moving the microscope section 7 rightward, the control section 38 outputs, after time $T_{33}$, control signals to various sections to drive various joint sections as needed to move the microscope section 7 rightward. In this instance, the control section 38 provides control such that the speed for moving the microscope section 7 increases with an increase in the depression amount of the foot switch 92 (with a decrease in the analog value).

Thereafter, when the foot switch 92 is released at time $T_{34}$, the microscope section 7 stops moving.

When the foot switch 92 is stepped on again at time $T_{35}$ within a preset range of time (period $R_T$) after time $T_{34}$, the control section 38 resumes moving the microscope section 7. In this instance, the control section 38 moves the microscope section 7 ("Leftward" in this case) in a direction opposite to the direction in which the microscope section 7 moved before foot switch re-depression. When moving the microscope section 7 in the opposite direction, the third embodiment moves the microscope section 7 at a constant speed without regard to the depression amount of the foot switch 92. The speed to be set in this instance is, for example, the maximum or minimum controllable speed, 50% of the maximum speed, or the maximum or minimum speed used for the last driving. It should be noted that the maximum controllable speed is set in the example depicted in FIG. 5.

Thereafter, when the foot switch 92 is released at time $T_{36}$, the microscope section 7 stops moving.

The third embodiment, which has been described above, receives a voice input from the microphone 91 in a state where the foot switch 92 is depressed, and executes processing based on the result of recognition. Thereafter, the third embodiment maintains the processing based on the recognition result while the foot switch 92 is depressed, and stops the processing when the foot switch 92 is released. Further, when the foot switch 92 is depressed again within the preset range of time (period $R_T$), the third embodiment executes a process that is the reverse of the preceding process. According to the third embodiment, the processing performed during a period between the start of voice recognition and the stop of the processing is collectively controlled within the control device 3 (which controls the microscope section 7 and the support section 6) upon depression of the foot switch 92. This makes it possible to adopt a simple configuration, complete the processing ranging from voice recognition to driving based on the voice recognition within a short period of time, and easily stop the processing. Additionally, the third embodiment executes a reverse process upon re-depression of the foot switch 92. Therefore, the processing can be fine-tuned simply by operating the foot switch 92.

Fourth Embodiment

Figure 6:
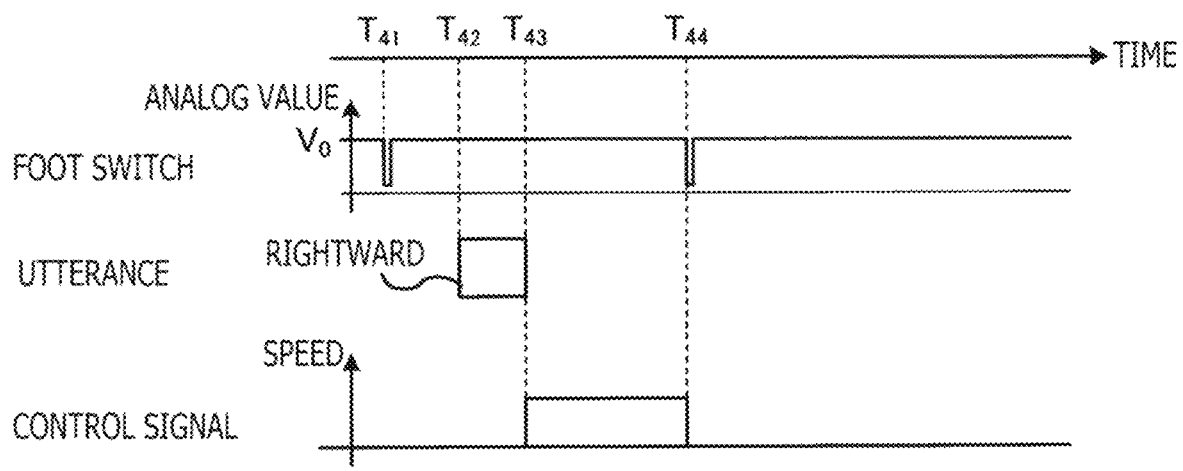
FIG. 6 is a timing diagram illustrating an example of the driving process that is performed by using the medical observation system according to a fourth embodiment of the present disclosure.

A fourth embodiment will now be described with reference to FIG. 6. FIG. 6 is a timing diagram illustrating an example of the driving process that is performed by using the medical observation system according to the fourth embodiment. The configuration of the medical observation system according to the fourth embodiment is the same as that of the earlier-described medical observation system 1 according to the first embodiment, and will not be redundantly described. The following describes the difference in processing from the first embodiment.

Upon detecting that the foot switch 92 is depressed (stepped on), the foot switch input reception section 35 outputs an analog value based on the depression amount to the control section 38. In the example of FIG. 6, the user steps on the foot switch 92 at time $T_{41}$ and immediately releases it. Therefore, the input value (analog value) inputted by the foot switch 92 temporarily decreases from the initial value ($V_0$) and then returns to the initial value ($V_0$).

Upon detecting that the foot switch 92 is depressed at time $T_{41}$, the control section 38 starts performing voice recognition processing by using the microphone 91. The user steps on the foot switch 92, and then inputs a voice to the microphone 91. In the example depicted in FIG. 6, the user inputs "Rightward" to the microphone 91.

When "Rightward" is inputted to the microphone 91 at time $T_{42}$, during a period until time $T_{43}$, the voice recognition section 32 performs recognition processing, and the recognized-information processing section 33 determines the processing to be executed.

The recognized-information processing section 33 determines the processing to be executed. In this instance, when the determined processing is for moving the microscope section 7 rightward, the control section 38 outputs, after time $T_{43}$, control signals to various sections to drive various joint sections as needed to move the microscope section 7 rightward. In this case, the control section 38 moves the microscope section 7 at a constant speed. The constant speed is set in a manner similar to that of the third embodiment, which has been described earlier.

Thereafter, upon detecting that the foot switch 92 is depressed at time $T_{44}$, the control section 38 stops the movement of the microscope section 7.

As described above, the fourth embodiment is configured such that, in a case where the analog value inputted when the foot switch 92 is stepped on changes to a value other than the initial value $V_0$, the control section 38 detects a first change and starts voice recognition processing. Meanwhile, in a case where the analog value inputted upon depression of the foot switch 92 changes again to a value other than the initial value $V_0$, the control section 38 detects a second change and stops processing based on voice recognition.

The fourth embodiment, which has been described above, receives a voice input from the microphone 91 upon detecting the depression of the foot switch 92, and executes processing based on the result of recognition. Thereafter, the fourth embodiment maintains the processing based on the recognition result, and stops the processing upon detecting re-depression of the foot switch 92. According to the fourth embodiment, the processing performed during a period between the start of voice recognition and the stop of the processing is collectively controlled within the control device 3 (which controls the microscope section 7 and the support section 6) upon depression of the foot switch 92, which acts as a trigger. This makes it possible to adopt a simple configuration, complete the processing ranging from voice recognition to driving based on the voice recognition within a short period of time, and easily stop the processing.

Fifth Embodiment

Figure 7:
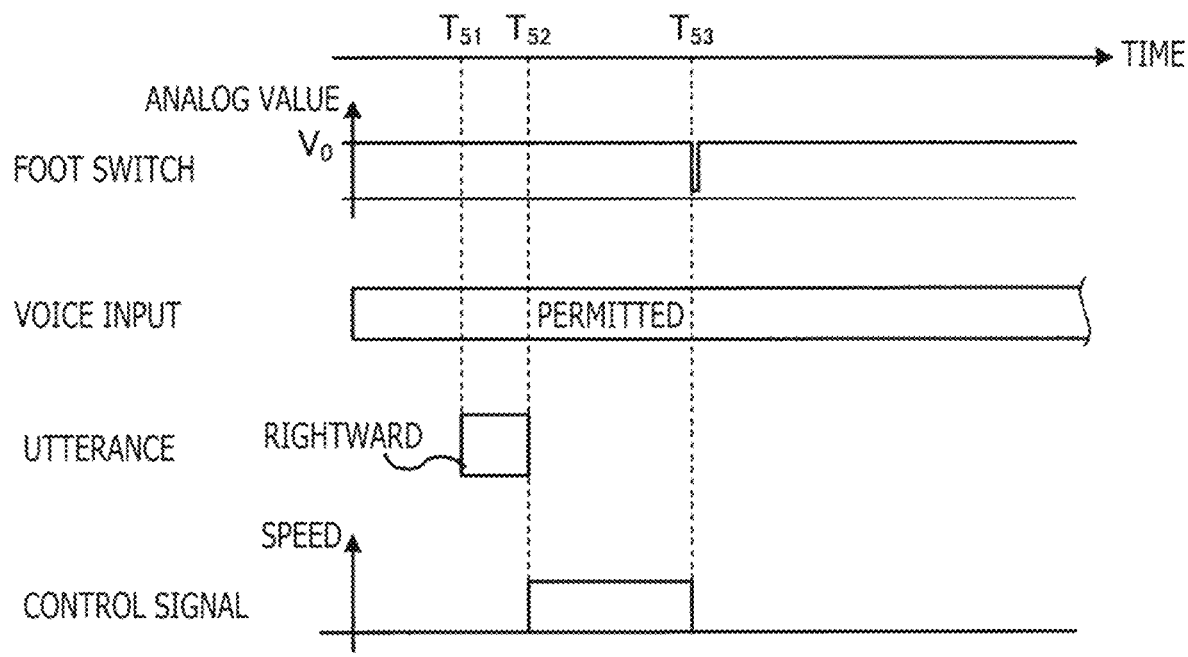
FIG. 7 is a timing diagram illustrating an example of the driving process that is performed by using the medical observation system according to a fifth embodiment of the present disclosure.

A fifth embodiment will now be described with reference to FIG. 7. FIG. 7 is a timing diagram illustrating an example of the driving process that is performed by using the medical observation system according to the fifth embodiment. The configuration of the medical observation system according to the fifth embodiment is the same as that of the earlier-described medical observation system 1 according to the first embodiment, and will not be redundantly described. The following describes the difference in processing from the first embodiment.

In the fifth embodiment, voice input reception is in a state where it is constantly permitted. More specifically, unlike the earlier-described first to fourth embodiments, which determine, based on depression of the foot switch 92, whether or not to process a voice input, the fifth embodiment constantly permits voice recognition processing to be performed on an inputted voice.

When "Rightward" inputted to the microphone 91 at time $T_{51}$, during a period until time $T_{52}$, the control section 38 causes the voice recognition section 32 to perform recognition processing and causes the recognized-information processing section 33 to determine the processing to be executed.

The recognized-information processing section 33 determines the processing to be executed. In this instance, when the determined processing is for moving the microscope section 7 rightward, the control section 38 outputs, after time $T_{52}$, control signals to various sections to drive various joint sections as needed to move the microscope section 7 rightward. In this case, the control section 38 moves the microscope section 7 at a constant speed. The constant speed is set in a manner similar to that of the third embodiment, which has been described earlier.

Thereafter, upon detecting that the foot switch 92 is depressed at time $T_{53}$, the control section 38 stops the movement of the microscope section 7. The fifth embodiment stops the movement of the microscope section 7 immediately after detecting the depression of the foot switch 92.

The fifth embodiment, which has been described above, receives a voice input from the microphone 91 and executes processing based on the result of recognition. Thereafter, the fifth embodiment maintains the processing based on the recognition result, and stops the processing upon detecting the depression of the foot switch 92. According to the fifth embodiment, the processing performed during a period between the start of voice recognition and the stop of the processing is collectively controlled within the control device 3 (which controls the microscope section 7 and the support section 6). This makes it possible to complete the processing ranging from voice recognition to driving based on the voice recognition within a short period of time by using a simple configuration, and easily stop the processing.

(Modification of Fifth Embodiment)

Figure 8:
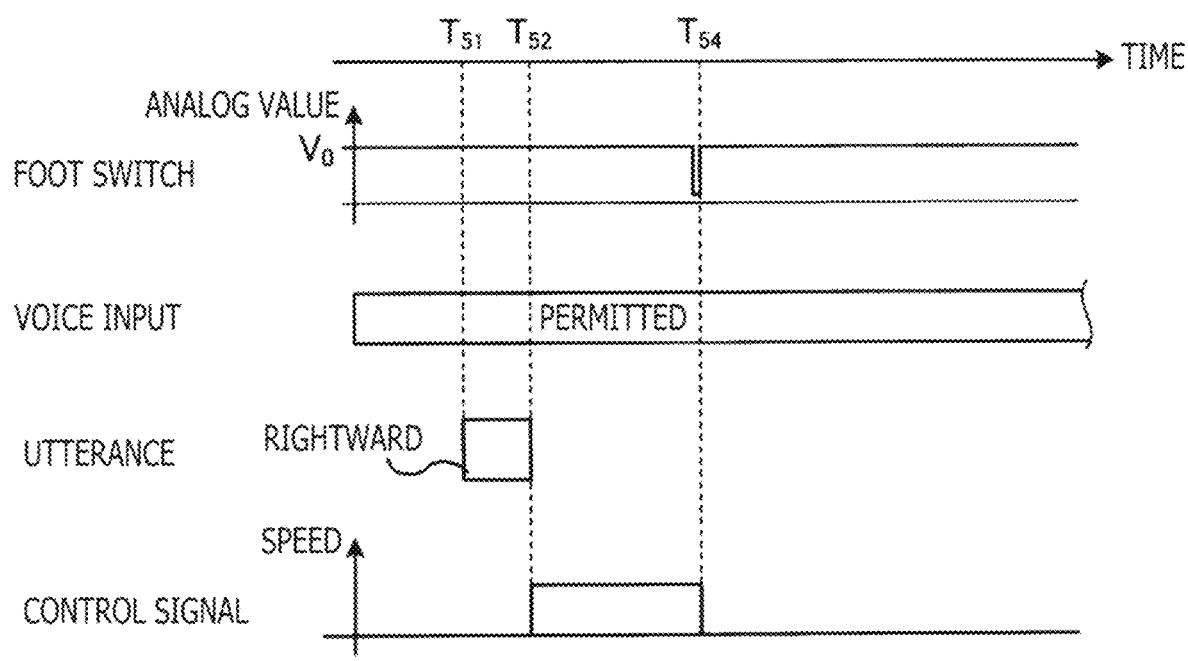
FIG. 8 is a timing diagram illustrating an example of the driving process that is performed by using the medical observation system according to a modification of the fifth embodiment.

A modification of the fifth embodiment will now be described with reference to FIG. 8. FIG. 8 is a timing diagram illustrating an example of the driving process that is performed by using the medical observation system according to the modification of the fifth embodiment. In the present modification, voice input reception is in a state where it is constantly permitted, as is the case with the fifth embodiment.

When "Rightward" inputted to the microphone 91 at time $T_{51}$, during a period until $T_{52}$, the control section 38 causes the voice recognition section 32 to perform recognition processing and causes the recognized-information processing section 33 to determine the processing to be executed.

The recognized-information processing section 33 determines the processing to be executed. In this instance, when the determined processing is for moving the microscope section 7 rightward, the control section 38 outputs, after time $T_{52}$, control signals to various sections to drive various joint sections as needed to move the microscope section 7 rightward. In this case, the control section 38 moves the microscope section 7 at a constant speed. The constant speed is set in a manner similar to that of the third embodiment, which has been described earlier.

Thereafter, upon detecting that the foot switch 92 is depressed, the control section 38 stops the movement of the microscope section 7. The present modification stops the movement of the microscope section 7 immediately after the foot switch 92 is released at time $T_{54}$.

The modification described above receives a voice input from the microphone 91 and executes processing based on the result of recognition. Thereafter, the modification maintains the processing based on the recognition result, and stops the processing upon detecting the depression of the foot switch 92. According to the modification, the processing performed during a period between the start of voice recognition and the stop of processing is collectively controlled within the control device 3 (which controls the microscope section 7 and the support section 6). This makes it possible to adopt a simple configuration, complete the processing ranging from voice recognition to driving based on the voice recognition within a short period of time, and easily stop the processing.

Sixth Embodiment

Figure 9:
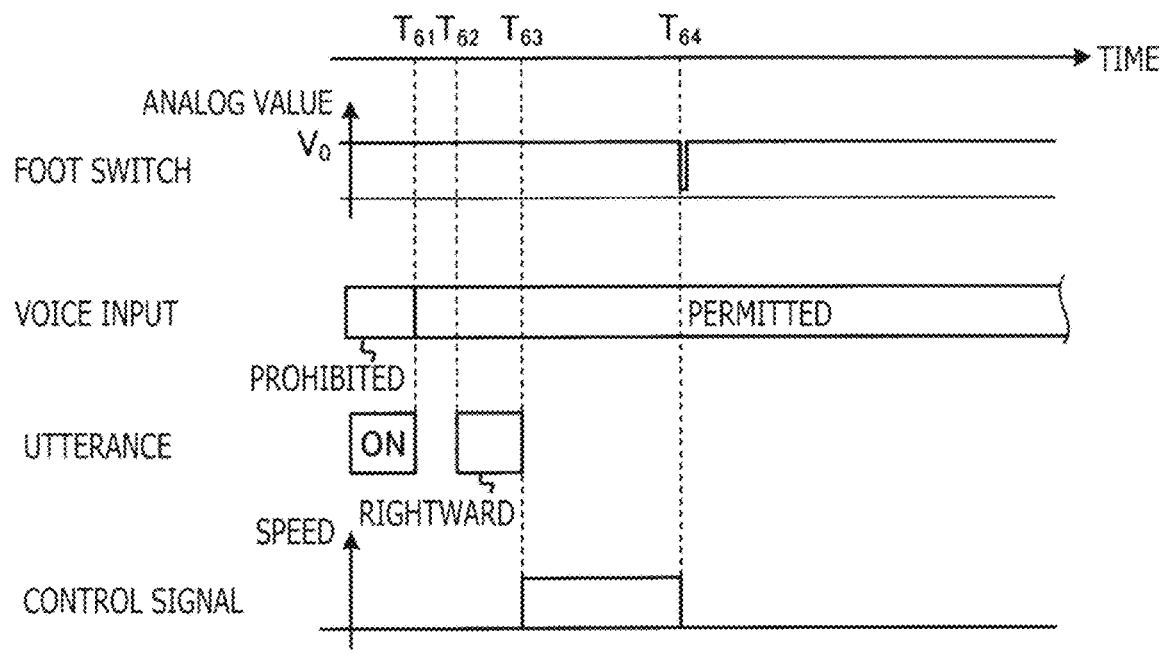
FIG. 9 is a timing diagram illustrating an example of the driving process that is performed by using the medical observation system according to a sixth embodiment of the present disclosure.

A sixth embodiment will now be described with reference to FIG. 9. FIG. 9 is a timing diagram illustrating an example of the driving process that is performed by using the medical observation system according to the sixth embodiment. The configuration of the medical observation system according to the sixth embodiment is the same as that of the earlier-described medical observation system 1 according to the first embodiment, and will not be redundantly described. The following describes the difference in processing from the first embodiment.

The sixth embodiment permits voice recognition processing related to driving in a case where a word indicated by a recognized voice or a word sequence, that is, a combination of a plurality of words, matches a preset word or word sequence. More specifically, unlike the earlier-described first to fourth embodiments, which start the voice recognition processing based on depression of the foot switch 92, the sixth embodiment enables recognition processing on an inputted voice after recognition based on voice input. In this instance, a word, such as "ON" or "Start," may be used as the word for permitting voice recognition, and a word sequence, such as "Enable voice recognition," may be used as the word sequence for permitting voice recognition. It should be noted that the word is assumed to include, for example, a postpositional particle and an auxiliary verb. The word or word sequence for indicating the permission of the voice recognition processing corresponds to first recognized information. The sixth embodiment is described below with reference to an example where "ON" is inputted.

When "ON" is inputted to the microphone 91 at time $T_{61}$, the control section 38 permits the voice recognition section 32 to perform recognition processing and the recognized-information processing section 33 to execute processing.

Thereafter, when "Rightward" is inputted to the microphone 91 at time $T_{62}$, during a period until time $T_{63}$, the control section 38 causes the voice recognition section 32 to perform recognition processing and causes the recognized-information processing section 33 to determine the processing to be executed.

The recognized-information processing section 33 determines the processing to be executed. In this instance, when the determined processing is for moving the microscope section 7 rightward, the control section 38 outputs, after time $T_{63}$, control signals to various sections to drive various joint sections as needed to move the microscope section 7 rightward. In this case, the control section 38 moves the microscope section 7 at a constant speed. The constant speed is set in a manner similar to that of the third embodiment, which has been described earlier.

Thereafter, upon detecting that the foot switch 92 is depressed at time $T_{64}$, the control section 38 stops the movement of the microscope section 7. The sixth embodiment stops the movement of the microscope section 7 immediately after detecting the depression of the foot switch 92.

The sixth embodiment, which has been described above, receives a voice input from the microphone 91 and executes processing based on the result of recognition. Thereafter, the sixth embodiment maintains the processing based on the recognition result, and stops the processing upon detecting the depression of the foot switch 92. According to the sixth embodiment, the processing performed during a period between the start of voice recognition and the stop of the processing is collectively controlled within the control device 3 (which controls the microscope section 7 and the support section 6). This makes it possible to adopt a simple configuration, complete the processing ranging from voice recognition to driving based on the voice recognition within a short period of time, and easily stop the processing.

(Modification of Sixth Embodiment)

Figure 10:
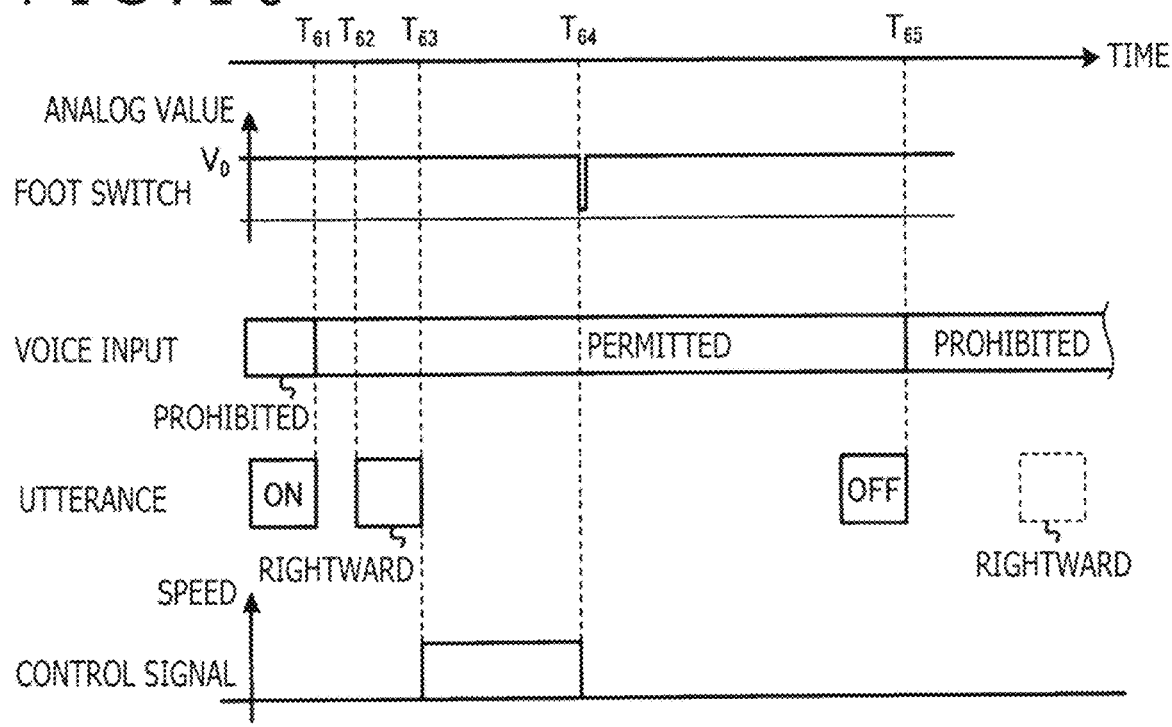
FIG. 10 is a timing diagram illustrating an example of the driving process that is performed by using the medical observation system according to a modification of the sixth embodiment.

A modification of the sixth embodiment will now be described with reference to FIG. 10. FIG. 10 is a timing diagram illustrating an example of the driving process that is performed by using the medical observation system according to the modification of the sixth embodiment. As is the case with the sixth embodiment, the present modification permits recognition processing on an inputted voice according to a preset word or an inputted sentence.

When "ON" is inputted to the microphone 91 at time $T_{61}$, the control section 38 permits the voice recognition section 32 to perform recognition processing and the recognized-information processing section 33 to execute processing.

Thereafter, when "Rightward" is inputted to the microphone 91 at time $T_{62}$, during a period until time $T_{63}$, the control section 38 causes the voice recognition section 32 to perform recognition processing and causes the recognized-information processing section 33 to determine the processing to be executed.

The recognized-information processing section 33 determines the processing to be executed. In this instance, when the determined processing is for moving the microscope section 7 rightward, the control section 38 outputs, after time $T_{63}$, control signals to various sections to drive various joint sections as needed to move the microscope section 7 rightward. In this case, the control section 38 moves the microscope section 7 at a constant speed. The constant speed is set in a manner similar to that of the third embodiment, which has been described earlier.

Thereafter, upon detecting that the foot switch 92 is depressed at time $T_{64}$, the control section 38 stops the movement of the microscope section 7.

When "OFF" is inputted to the microphone 91 at time $T_{65}$ after the stop of driving by the foot switch 92, the control section 38 prohibits the voice recognition section 32 from performing later recognition processing. This disables the result of recognition that is specified by a voice input. Alternatively, for example, "Terminate" or "Disable voice recognition" may be set. The word or word sequence specifying the prohibition of voice recognition processing corresponds to second recognized information. During a period during which voice recognition processing is prohibited, only the recognition of a word or word sequence enabling voice recognition and the execution of processing based on such recognition (voice recognition enable setting) are enabled.

The modification described above receives a voice input from the microphone 91 and executes processing based on the result of recognition. Thereafter, the modification maintains the processing based on the recognition result, and stops the processing upon detecting the depression of the foot switch 92. According to the modification, the processing performed during a period between the start of voice recognition and the stop of the processing is collectively controlled within the control device 3 (which controls the microscope section 7 and the support section 6). This makes it possible to adopt a simple configuration, complete the processing ranging from voice recognition to driving based on the voice recognition within a short period of time, and easily stop the processing.

Seventh Embodiment

Figure 11:
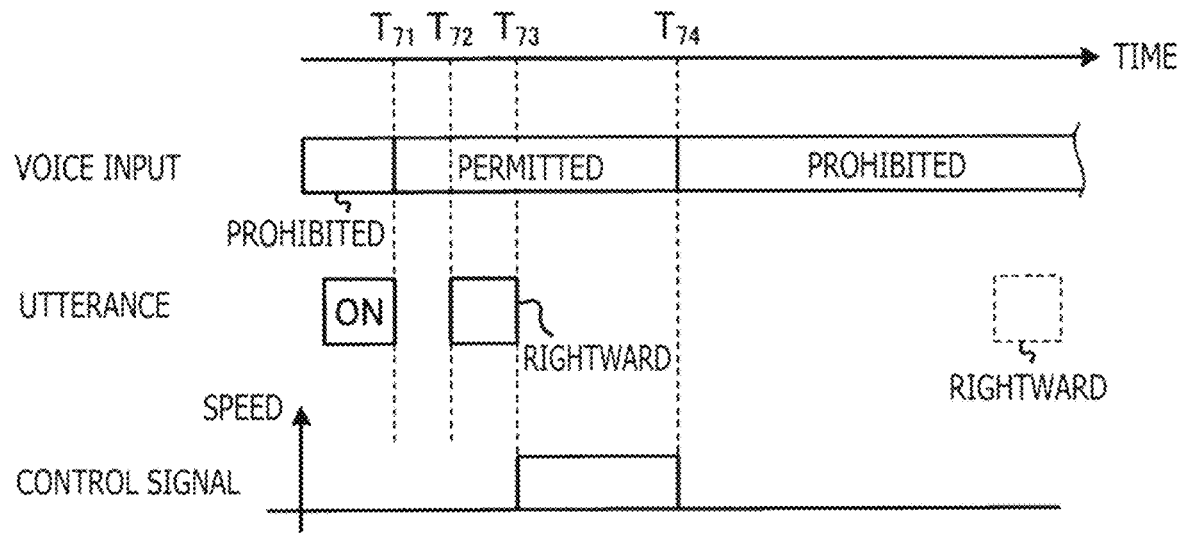
FIG. 11 is a timing diagram illustrating an example of the driving process that is performed by using the medical observation system according to a seventh embodiment of the present disclosure.

A seventh embodiment will now be described with reference to FIG. 11. FIG. 11 is a timing diagram illustrating an example of the driving process that is performed by using the medical observation system according to the seventh embodiment. The configuration of the medical observation system according to the seventh embodiment is the same as that of the earlier-described medical observation system 1 according to the first embodiment, and will not be redundantly described. The following describes the difference in processing from the first embodiment.

Based on a preset word or word sequence, the seventh embodiment permits voice recognition processing related to driving, as is the case with the sixth embodiment. Further, when a preset period of time elapses after the start of permission of voice recognition processing or the stop of driving of the microscope section 7, the control section 38 prohibits the voice recognition processing again.

It should be noted that the seventh embodiment stops the movement of the microscope section 7 when a preset period of time elapses after the start of movement. The seventh embodiment prohibits the voice recognition processing again when a preset period of time elapses after permission or when a preset period of time elapses after the stop of driving of the microscope section 7.

When "ON" is inputted to the microphone 91 at time $T_{71}$, the control section 38 permits the voice recognition section 32 to perform recognition processing and the recognized-information processing section 33 to execute processing.

Thereafter, when "Rightward" is inputted to the microphone 91 at time $T_{72}$, during a period until time $T_{73}$, the control section 38 causes the voice recognition section 32 to perform recognition processing and causes the recognized-information processing section 33 to determine the processing to be executed.

The recognized-information processing section 33 determines the processing to be executed. In this instance, when the determined processing is for moving the microscope section 7 rightward, the control section 38 outputs, after time $T_{73}$, control signals to various sections to drive various joint sections as needed to move the microscope section 7 rightward. In this case, the control section 38 moves the microscope section 7 at a constant speed. The constant speed is set in a manner similar to that of the third embodiment, which has been described earlier.

Thereafter, at time $T_{74}$, which arrives when a preset period of time elapses after time $T_{73}$, the control section 38 stops the movement of the microscope section 7, and prohibits the voice recognition section 32 to perform later recognition processing. In the seventh embodiment, a signal indicating the elapse of time corresponds to the second operation signal.

The seventh embodiment, which has been described above, receives a voice input from the microphone 91 and executes processing based on the result of recognition. Thereafter, the seventh embodiment maintains the processing based on the recognition result, and stops the processing when a preset period of time elapses. According to the seventh embodiment, the processing performed during a period between the start of voice recognition and the stop of the processing is collectively controlled within the control device 3 (which controls the microscope section 7 and the support section 6). This makes it possible to adopt a simple configuration, complete the processing ranging from voice recognition to driving based on the voice recognition within a short period of time, and easily stop the processing.

It should be noted that the control section 38 in the seventh embodiment may prohibit voice input after stopping the movement of the microscope section 7 at time $T_{74}$.

Eighth Embodiment

Figure 12:
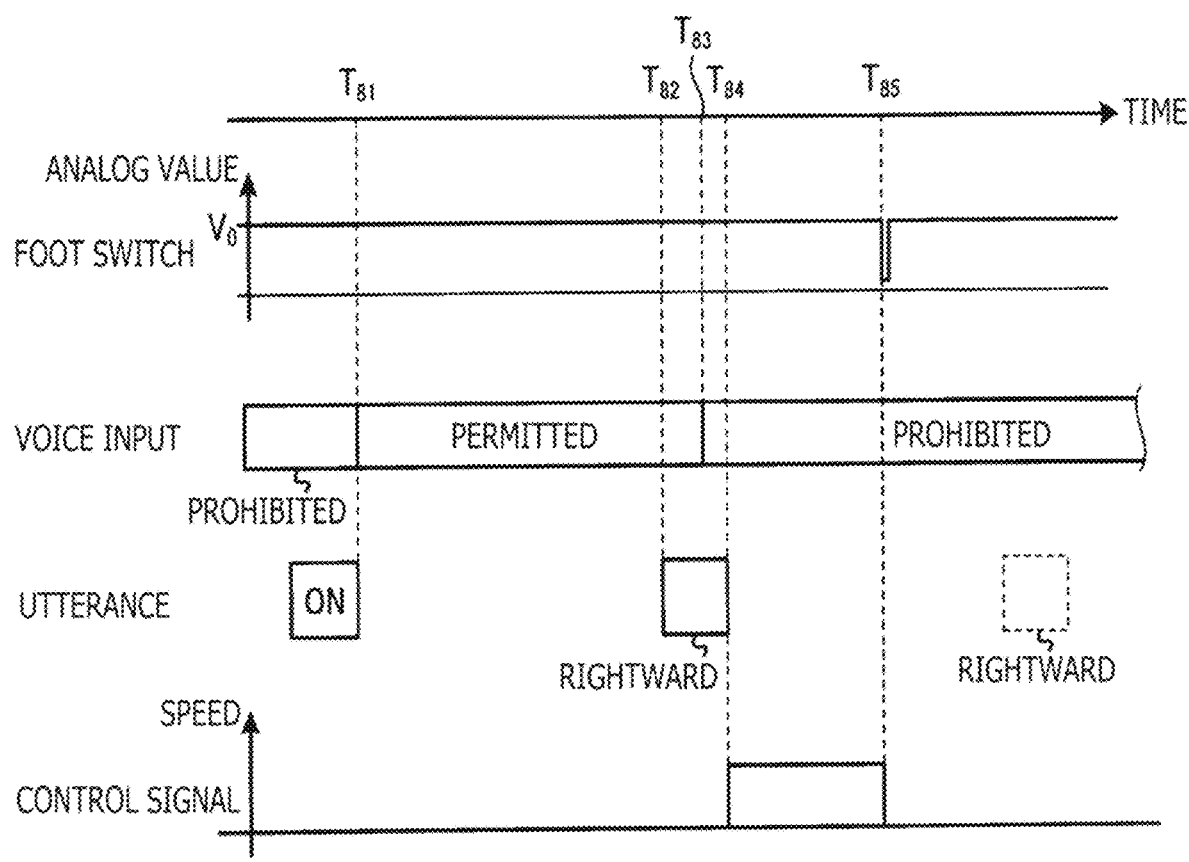
FIG. 12 is a timing diagram illustrating an example of the driving process that is performed by using the medical observation system according to an eighth embodiment of the present disclosure.

An eighth embodiment will now be described with reference to FIG. 12. FIG. 12 is a timing diagram illustrating an example of the driving process that is performed by using the medical observation system according to the eighth embodiment. The configuration of the medical observation system according to the eighth embodiment is the same as that of the earlier-described medical observation system 1 according to the first embodiment, and will not be redundantly described. The following describes the difference in processing from the first embodiment.

Based on a preset word or word sequence, the eighth embodiment permits voice recognition processing related to driving, as is the case with the sixth embodiment. Further, when a preset period of time elapses after the start of permission of voice recognition processing or the stop of driving of the microscope section 7, the control section 38 prohibits the voice recognition processing again, as is the case with the seventh embodiment.

When "ON" is inputted to the microphone 91 at time $T_{81}$, the control section 38 permits the voice recognition section 32 to perform recognition processing and the recognized-information processing section 33 to execute processing.

Thereafter, when "Rightward" is inputted to the microphone 91 at time $T_{82}$, during a period until time $T_{84}$, the control section 38 causes the voice recognition section 32 to perform recognition processing and causes the recognized-information processing section 33 to determine the processing to be executed. In this instance, setup is performed so as to prohibit voice recognition processing at time $T_{83}$, which is earlier than time $T_{84}$. Even during a period of time during which prohibition is set, the control section allows the recognized-information processing section 33 to continue with processing as far as a relevant voice input is started during a period during which voice recognition processing is permitted.

The recognized-information processing section 33 determines the processing to be executed. In this instance, when the determined processing is for moving the microscope section 7 rightward, the control section 38 outputs, after time $T_{84}$, control signals to various sections to drive various joint sections as needed to move the microscope section 7 rightward. In this case, the control section 38 moves the microscope section 7 at a constant speed. The constant speed is set in a manner similar to that of the third embodiment, which has been described earlier.

Thereafter, upon detecting that the foot switch 92 is depressed at time $T_{85}$, the control section 38 stops the movement of the microscope section 7. As described above, even during a period during which voice recognition processing is prohibited, the eighth embodiment continues with stop processing based on an input from the foot switch 92. Enabling an instruction for stopping driving during a period during which voice recognition processing is prohibited, is useful particularly in an emergency where, for example, a malfunction is encountered or the microscope section 7 is about to come into contact with other equipment or a patient. It should be noted that driving of the microscope section 7 may be stopped when a preset period of time elapses after the start of driving. Further, the driving of the microscope section 7 may be stopped after time $T_{83}$.

The eighth embodiment, which has been described above, receives a voice input from the microphone 91 and executes processing based on the result of recognition. Thereafter, the eighth embodiment maintains the processing based on the recognition result, and stops the processing upon detecting the depression of the foot switch 92. According to the eighth embodiment, the processing performed during a period between the start of voice recognition and the stop of the processing is collectively controlled within the control device 3 (which controls the microscope section 7 and the support section 6). This makes it possible to adopt a simple configuration, complete the processing ranging from voice recognition to driving based on the voice recognition within a short period of time, and easily stop the processing.

(Modification of Eighth Embodiment)

Figure 13:
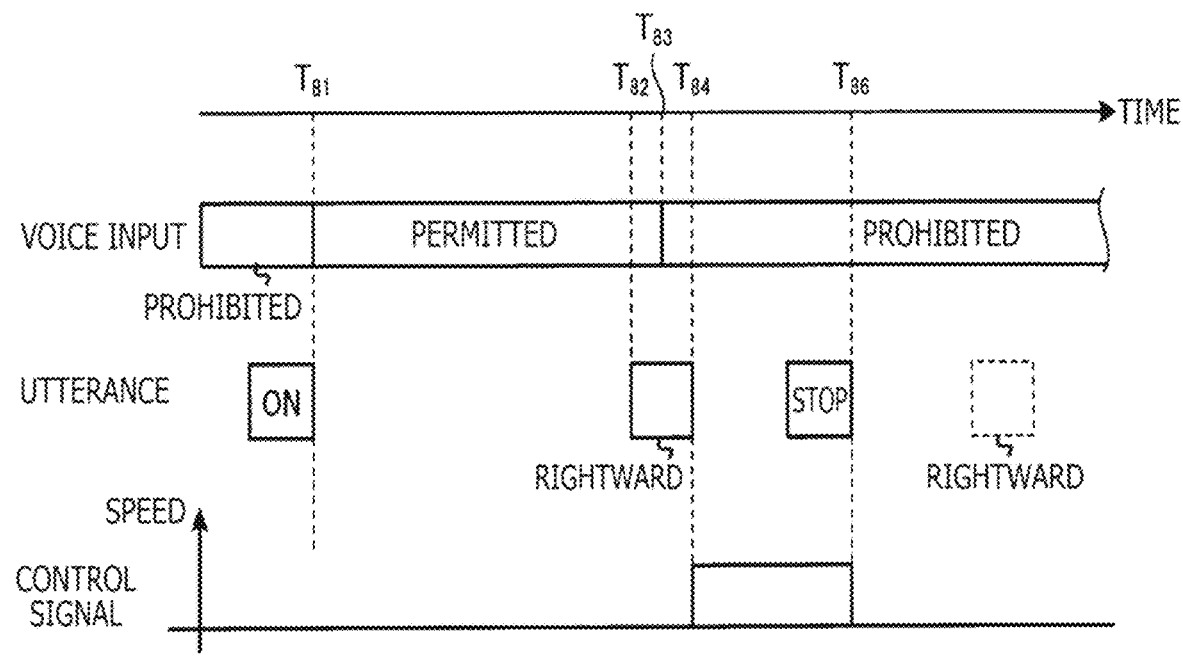
FIG. 13 is a timing diagram illustrating an example of the driving process that is performed by using the medical observation system according to a modification of the eighth embodiment.

A modification of the eighth embodiment will now be described with reference to FIG. 13. FIG. 13 is a timing diagram illustrating an example of the driving process that is performed by using the medical observation system according to the modification of the eighth embodiment. As is the case with the eighth embodiment, the present modification continuously processes on a voice whose input is started during a period during which voice recognition processing is permitted. Further, the present modification stops the movement of the microscope section 7 according to voice recognition.

When "ON" is inputted to the microphone 91 at time $T_{81}$, the control section 38 permits the voice recognition section 32 to perform recognition processing and the recognized-information processing section 33 to execute processing.

Thereafter, when "Rightward" is inputted to the microphone 91 at time $T_{82}$, during a period until time $T_{84}$, the control section 38 causes the voice recognition section 32 to perform recognition processing and causes the recognized-information processing section 33 to determine the processing to be executed. In this instance, in a case where setup is performed to prohibit voice recognition processing at time $T_{83}$, which is earlier than time $T_{84}$, the control section 38 allows the recognized-information processing section 33 to continue with processing even during a period during which voice recognition processing is prohibited.

The recognized-information processing section 33 determines the processing to be executed. In this instance, when the determined processing is for moving the microscope section 7 rightward, the control section 38 outputs, after time $T_{84}$, control signals to various sections to drive various joint sections as needed to move the microscope section 7 rightward.

Thereafter, when "Stop" is voice-recognized at time $T_{86}$, the control section 38 stops the movement of the microscope section 7. As described above, even during a period during which voice recognition processing is prohibited, the present modification continuously performs recognition processing on a processing-related voice command during driving. In the present modification, the first operation signal and the second operation signal both act as a signal that is generated upon voice input and based on the same operation.

Enabling an instruction for processing during driving during a period during which voice recognition processing is prohibited, is useful particularly in an emergency where, for example, a malfunction is caused by a voice recognition error or the microscope section 7 is about to come into contact with other equipment or a patient. It should be noted that driving of the microscope section 7 may be stopped when a preset period of time elapses after the start of driving. Further, the driving of the microscope section 7 may be stopped after time $T_{83}$.

The modification described above receives a voice input from the microphone 91 and executes processing based on the result of recognition. Thereafter, the modification maintains the processing based on the recognition result, and stops the processing upon detecting a voice-recognized stop instruction. According to the modification, the processing performed during a period between the start of voice recognition and the stop of the processing is collectively controlled within the control device 3 (which controls the microscope section 7 and the support section 6). This makes it possible to adopt a simple configuration, complete the processing ranging from voice recognition to driving based on the voice recognition within a short period of time, and easily stop the processing.

Ninth Embodiment

Figure 14:
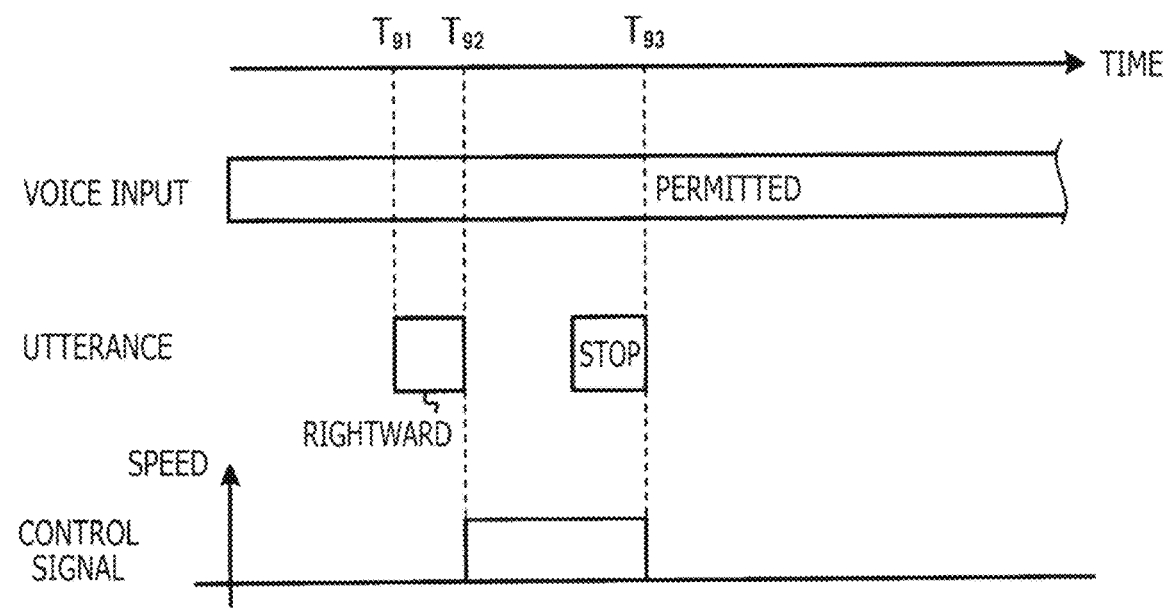
FIG. 14 is a timing diagram illustrating an example of the driving process that is performed by using the medical observation system according to a ninth embodiment of the present disclosure.

A ninth embodiment will now be described with reference to FIG. 14. FIG. 14 is a timing diagram illustrating an example of the driving process that is performed by using the medical observation system according to the ninth embodiment. The configuration of the medical observation system according to the ninth embodiment is the same as that of the earlier-described medical observation system 1 according to the first embodiment, and will not be redundantly described. The following describes the difference in processing from the first embodiment.

In the ninth embodiment, voice input reception is in a state where it is constantly permitted, as is the case with the fifth embodiment. Further, the control section 38 controls the driving start and stop of the microscope section 7 according to voice recognition.

When "Rightward" is inputted to the microphone 91 at time $T_{91}$, during a period until time $T_{92}$, the control section 38 causes the voice recognition section 32 to perform recognition processing and causes the recognized-information processing section 33 to determine the processing to be executed.

The recognized-information processing section 33 determines the processing to be executed. In this instance, when the determined processing is for moving the microscope section 7 rightward, the control section 38 outputs, after time $T_{92}$, control signals to various sections to drive various joint sections as needed to move the microscope section 7 rightward. In this case, the control section 38 moves the microscope section 7 at a constant speed. The constant speed is set in a manner similar to that of the third embodiment, which has been described earlier.

Thereafter, when "Stop" is voice-recognized at time $T_{93}$, the control section 38 stops the movement of the microscope section 7.

The ninth embodiment, which has been described above, receives a voice input from the microphone 91 and executes processing based on the result of recognition. Thereafter, the ninth embodiment maintains the processing based on the recognition result, and stops the processing upon detecting a voice-recognized stop instruction. According to the ninth embodiment, the processing performed during a period between the start of voice recognition and the stop of the processing is collectively controlled within the control device 3 (which controls the microscope section 7 and the support section 6). This makes it possible to adopt a simple configuration, complete the processing ranging from voice recognition to driving based on the voice recognition within a short period of time, and easily stop the processing.

While the embodiments for practicing the present invention have been described, the present invention is not limited to the foregoing embodiments. For example, it is sufficient that the support section 6 alternatively includes at least one set of two arm sections and one joint section adapted to pivotally couple one arm section to the other arm section.

It should be noted that the first to fourth embodiments have been described with reference to an example where the processing performed during a period between the start of voice recognition and the stop of driving is controlled by operating the foot switch 92. However, an alternative configuration may be adopted to use, for example, a hand-operated switch instead of a foot-operated switch. Further, the foot switch 92 may be substituted, for example, by a pressure sensor or an acceleration sensor.

Further, the first to fourth embodiments have been described with reference to an example where the input value inputted by depressing the foot switch 92 is smaller than the initial value. However, an alternative configuration may be adopted such that the input value is greater than the initial value depending on the amount of depression. Another alternative configuration may be adopted such that the foot switch 92 outputs a digital value, such as a binary or ternary value, instead of an analog value.

Further, the first to fourth embodiments may alternatively be configured such that the control section 38 keeps the microphone 91 on during a period between the start of voice recognition and the stop of driving, and keeps the microphone 91 off during the other period. This prevents an utterance from being inputted during a period other than a voice recognition period. Another alternative is to raise the input volume of the microphone 91 during the voice recognition period, and lower the input volume of the microphone 91 or mute (silence) the microphone 91 during a period other than the voice recognition period.

Further, the first to fourth embodiments have been described with reference to an example where the microphone 91 and the foot switch 92 are wiredly connected to the control device 3. However, an alternative configuration may be adopted such that the microphone 91 and the foot switch 92 are wirelessly connected to the control device 3. It should also be noted that the observation apparatus 2 and the control device 3 may be connected either wirelessly or wiredly.

Further, the first to fourth embodiments have been described with reference to an example where one set of the microphone 91 and the foot switch 92 is incorporated. However, a plurality of sets of the microphone 91 and the foot switch 92 may be incorporated. For example, an alternative is to provide a first set for a surgeon, a second set for an assistant surgeon, and a third set for a nurse, and define the priority level of each operation input.

Further, the first to fourth embodiments may alternatively be configured such that, upon recognizing an utterance, the control device 3 emits light or sound from the output section 36 to notify the user that the utterance is recognized. It should also be noted that the display device 4 may display a message indicative of utterance recognition.

Further, an alternative configuration may be adopted such that a medical observation apparatus is hung from the ceiling of a room where the medical observation apparatus is installed.

Further, the first to fourth embodiments have been described with reference to an example where the control device 3 is disposed separately from the observation apparatus 2. However, the control device 3 may be built in the base section 5.

Further, the first to fourth embodiments have been described with reference to an example where the support section 6 retains the microscope section 7. However, the support section 6 may retain, instead of the microscope section 7, a member that is configured to be able to capture an image. For example, the leading end of the support section 6 may be adapted to retain a rigid endoscope or a flexible endoscope. In a case where the support section 6 retains an endoscope, the base section 5 and the support section 6 function as an endoscope holder.

As described above, the present invention may include, for example, various embodiments without departing from the technical ideas described in the appended claims.

INDUSTRIAL APPLICABILITY

As described above, the control device and the medical observation system according to the present disclosure are useful in adopting a simple configuration, completing processing ranging from voice recognition to driving based on the voice recognition within a short period of time, and easily stopping the driving.

REFERENCE SIGNS LIST

1: Medical observation system
2: Medical observation apparatus
3: Control device
4: Display device
5: Base section
6: Support section
7: Microscope section
8: Light source device
11: First joint section
12: Second joint section
13: Third joint section
14: Fourth joint section
15: Fifth joint section
16: Sixth joint section
21: First arm section
22: Second arm section
23: Third arm section
24: Fourth arm section
25: Fifth arm section
31: Image processing section
32: Voice recognition section
33: Recognized-information processing section
34: Input section
35: Foot switch input reception section
36: Output section
37: Storage section
38: Control section
91: Microphone
92: Foot switch

The invention claimed is:

1. A control device for electrically controlling a medical observation apparatus that captures an image of an observation target, the control device comprising:
   circuitry configured to
      receive an input value as an operation signal of a switch,
      start voice recognition processing based on a voice inputted from outside in a case where the input value is changed from an initial value of the switch to a value other than the initial value,
      determine processing to be executed by the medical observation apparatus based on a result of the voice recognition processing,
      cause the medical observation apparatus to execute the processing that is determined,
      cause the medical observation apparatus to stop the processing in a case where the input value is changed back to the initial value, and
      cause the medical observation apparatus to execute reverse processing that is reverse of the processing that is stopped, in a case where the input value is changed again from the initial value during a preset period after the medical observation apparatus is caused to stop the processing.

2. The control device according to claim 1, wherein the circuitry is further configured to change driving speed of the medical observation apparatus according to the operation signal that is received.

3. The control device according to claim 1, wherein the circuitry is further configured to
   receive the operation signal that is outputted upon depression of the switch,
   cause the medical observation apparatus to continuously execute the processing, while the switch is continuously depressed, and
   cause the medical observation apparatus to stop the processing in a case where the switch is released.

4. The control device according to claim 1, wherein
   in a case where the result of the voice recognition processing agrees with first recognized information, the circuitry is further configured to enable later voice recognition processing, and
   in a case where the result of the voice recognition processing agrees with second recognized information, the circuitry is further configured to disable the later voice recognition processing.

5. The control device according to claim 1, wherein
   in a case where the result of the voice recognition processing agrees with first recognized information, the circuitry is further configured to enable later voice recognition processing, and
   after a preset period of time elapses since the voice recognition processing is enabled, the circuitry is further configured to disable a voice recognition result other than the first recognized information.

6. The control device according to claim 1, wherein
   based on the result of the voice recognition processing, the circuitry is further configured to determine a direction in which the medical observation apparatus moves an imaging area, and cause the medical observation apparatus to move the imaging area in the direction that is determined.

7. The control device according to claim 1, wherein
   based on the result of the voice recognition processing, the circuitry is further configured to determine image magnifying power of the medical observation apparatus and cause the medical observation apparatus to set the image magnifying power that is determined.

8. A medical observation system comprising:
   a medical observation apparatus that includes
      a microscope configured to capture a magnified image of an observation target, and
      a support that includes a plurality of arms and a plurality of joints rotatably connecting the plurality of arms and supports the microscope at a leading end of the support, the plurality of joints including actuators that cause relative movements of the plurality of arms to change a position of the microscope;
   a switch configured to output an operation signal based on an operation performed on the switch; and
   circuitry configured to
      receive an input value as the operation signal from the switch,
      start voice recognition processing based on a voice inputted from outside in a case where the input value is changed from an initial value of the switch to a value other than the initial value,
      determine processing to be executed by the medical observation apparatus based on a result of the voice recognition processing, the processing including at least changing the position of the microscope and cause the medical observation apparatus to execute the processing that is determined, cause the medical observation apparatus to stop the processing in a case where the input value is changed back to the initial value and cause the medical observation apparatus to execute reverse processing that is reverse of the processing that is stopped, in a case where the input value is changed again from the initial value during a preset period after the medical observation apparatus is caused to stop the processing.

\* \* \* \* \*